United States Patent [19]

Heimerl et al.

[11] Patent Number: 4,874,370
[45] Date of Patent: Oct. 17, 1989

[54] ADAPTER DEVICE FOR IRRIGATING THE INTESTINE

[75] Inventors: Albert Heimerl, Ammersbek; Hans-Adolf Brammer, Buchholz; Wolfgang Hofeditz, Hamburg, all of Fed. Rep. of Germany

[73] Assignee: Beiersdorf Aktiengesellschaft, Hamburg, Fed. Rep. of Germany

[21] Appl. No.: 165,877

[22] Filed: Mar. 9, 1988

Related U.S. Application Data

[63] Continuation of Ser. No. 932,966, Nov. 20, 1986, abandoned.

[30] Foreign Application Priority Data

Nov. 30, 1985 [DE] Fed. Rep. of Germany ....... 8533814

[51] Int. Cl.$^4$ .............................................. A61M 11/00
[52] U.S. Cl. ........................................ 604/93; 604/54;
604/174; 128/334 C; 285/4
[58] Field of Search .................... 604/8, 27–29,
604/36, 41, 42, 276, 277, 54, 56, 173, 174, 93,
96; 433/91, 96; 285/4; 384.4; 128/334 R, DIG.
25, 334 C, 335; 138/118.1, 120

[56] References Cited

U.S. PATENT DOCUMENTS

| 2,449,754 | 9/1948 | Seitz | 285/4 |
| 3,087,493 | 4/1963 | Schossow | 604/96 |
| 3,823,714 | 7/1974 | Waysilk | 604/28 |
| 3,937,224 | 2/1976 | Vecker | 604/227 |
| 4,340,037 | 7/1982 | Lewicky | 604/28 |
| 4,483,688 | 11/1984 | Akiyame | 604/265 |
| 4,637,814 | 1/1987 | Leiboff | 604/27 |

FOREIGN PATENT DOCUMENTS 022478 6/1987 European Pat. Off. .
2651175 5/1978 Fed. Rep. of Germany ...... 604/333

Primary Examiner—J. L. Kruter
Attorney, Agent, or Firm—Sprung, Horn, Kramer & Woods

[57] ABSTRACT

A device for irrigating the intestines that can be employed during surgery with an irrigating cannula for introducing a rinse and with a drain. To ensure irrigation during surgery of a section of intestine of any diameter upstream of the stenosis while avoiding any contamination of the operating field, the drain consists of an adapter connected germ-proof to a hose and of a plastic fastener securing the intestine to the adapter.

9 Claims, 2 Drawing Sheets

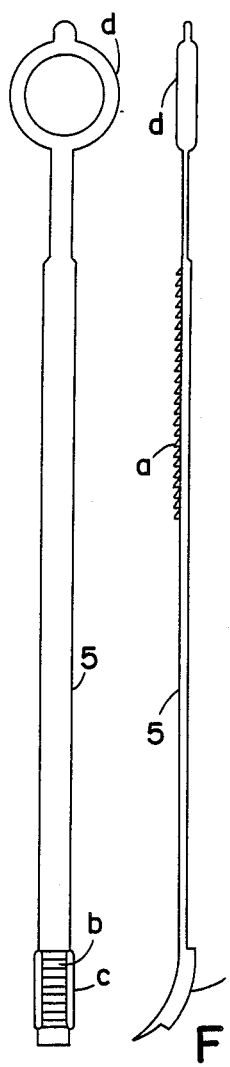
FIG.2A
FIG.2B
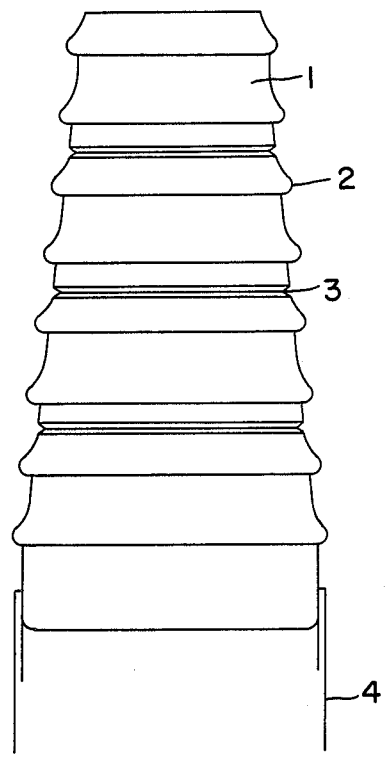
FIG.1

ADAPTER DEVICE FOR IRRIGATING THE INTESTINE

This is a continuation of Ser. No. 932,966, filed Nov. 20, 1986, now abandoned.

BACKGROUND OF THE INVENTION

The present invention relates to a device for irrigating the intestine that can be employed during surgery. An obstruction of the intestine, called an intestinal occlusion or ileus, can result either from functional disruptions of intestinal motility not due to any anatomical obstacle or from mechanical disruptions.

Free passage through the intestine can in the case of mechanical obstructions be restored only by surgery. In colonic ileus, which is frequently caused by a stenosing carcinoma, the acute process is usually preceded by several days of constipation. As the contents of the intestine continue to back up in the colon as a whole and in the small intestine as well, the patients develop symptoms of illness that in certain situations require emergency surgical intervention with very little warning. The usual preliminary several days' flushing and relief of the digestive tract to minimize as much as possible the invasion of germs from the thickly colonized intestinal lumen into the abdominal cavity during the operation is impossible in such an emergency.

Subject to the conditions of emergency resection of tumorous or otherwise stenosing sections of the intestine, attempts have previously been made, in cases wherein no fistula is created to relieve the intestine, to suction out the contents with intestinal aspirators inserted into the intestinal lumen. This method, however, does not satisfactorily flush out the intestine. Furthermore, previous tests of oral-to-aboral irrigation during surgery have exhibited no advantages due to the difficulty of removing the resulting waste liquid from the abdominal regions at risk.

SUMMARY OF THE INVENTION

The object of the present invention is to provide a device for irrigating the intestine that can be employed to ensure irrigation during surgery of the section of an intestine of any diameter upstream of the stenosis while avoiding any contamination of the operating field that would lead to the known and to the patient life-threatening consequences. The device is also intended to comply with waste-disposal guidelines (in accordance with German Federal Health Bulletin 9 [1985] for instance).

This object is attained in a device for irrigating the intestine that can be employed during surgery with an irrigating cannula for introducing a rinse and with a means of drainage by the improvement wherein the means of drainage consists of an adapter connected germ-proof to a hose and of a means of securing the intestine to the adapter. A preferred embodiment of the invention will now be specified with reference to the attached drawings, wherein

BRIEF DESCRIPTION OF THE DRAWINGS

FIG. 1 is a view of an adapter in accordance with the invention,

FIG. 2 is a top view and FIG. 2b is a side view of a securing strip or similar structure in accordance with the invention.

DETAILED DESCRIPTION OF THE PREFERRED EMBODIMENT

Figure 3:
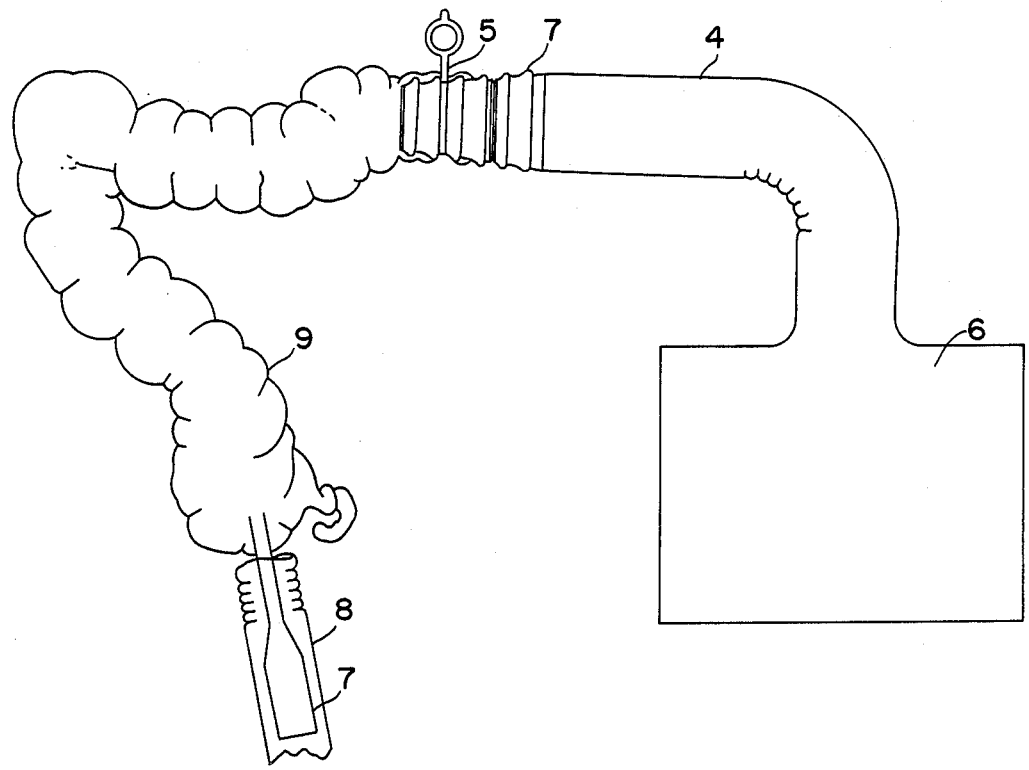
FIG. 3 illustrates the device in accordance with the invention in use.

The device consists of an adapter 1, securing strips 5 or similar structure, a drainage hose 4, a waste receiver 6, an irrigating cannula 7, and a length 8 of flexible plastic tubing around the cannula.

When the device is employed, an adapter is inserted with drainage hose 4 connected to it into the oral cuff of a section 9 of intestine upstream of the constriction and secured liquid-tight with strip 5 tightened around the outside of the section of intestine. Irrigating cannula 7 is inserted into the intestine through the appendix or through an incision farther oral, and the rinse is injected through the cannula. Waste picked up by the rinse is then drained into waste receiver 6, which is positioned next to the operating table, through drainage hose 4.

Adapter 1, which is in a practical way injection molded out of a physiologically compatible plastic, is preferably conical and has several trimming guides in the form of scores 3 so that it can be adapted for insertion into intestines of different diameter. Its inside diameters range from 10 mm at one end to 50 mm at the other, and its cross-section can be circular or elliptical. Its wall is approximately 2 mm thick. It has on its outer surface in a practical way one or more reinforcing beads 2 about 2 mm thick. The side of each bead that faces the body-proximal (tapering in) end of the adaptor can slope toward that end.

Drainage hose 4, which is preferably a length of flexible plastic tubing, is connected, generally cemented or welded, to the end of adaptor 1 with the longest diameter. Drainage hose 4 empties into waste receiver 6, which should be as strong and tight as possible for reasons of hygiene. The hose can be in one piece with the receiver for this purpose, in which case the receiver can be a plastic bag molded or welded onto the hose to create a germ-tight and integral drainage and receiver component.

To prevent contamination of the operating field at the end where irrigating cannula 7 is inserted into the intestine, the site of insertion is sealed off with length 8 of flexible plastic tubing that fits around the cannula and the area that it is inserted in. When the cannula is extracted, it travels back into the tubing, which prevents it from contaminating the operating field.

The section of intestine can be secured over adapter 1 with strips 5, each of which is wrapped around the intestine and adapter between two of the reinforcing beads 2. The securing strips can in a highly practical way consist of plastic rapid fasteners similar to those known in the packaging industry for use in baling. Strips of this type will secure the intestine to the adaptor liquid-tight and without slipping. The bands should be designed such that the intestine will be forced against the radially vertical side of the bead to ensure reliable drainage of the rinse.

FIG. 2 illustrates an especially practical embodiment of a securing strip. Once the strip has been positioned it is drawn into a loop with its teeth a engaging matching depressions b in a U-shaped channel c. The section that contains channel c curves back slightly to match the curve of the loop. A ring d functions as a tab for tightening the loop.

The present specification and claims are of course intended solely as illustrative of one or more potential embodiments of the invention and should not be construed as limiting it in any way. The invention may accordingly be adapted and modified in many ways without deviating from the theory behind it or exceeding its scope of application.

What is claimed is:

1. In combination, for irrigating the intestines during surgery, an irrigating cannula for connection to the intestines at one location, a conical apapter for connection to the intestines at a second location, the adapter having one or more trimming guides in the form of scores, means for securing the intestines to said adapter, and a hose connected to the adapter, whereby when said cannula, adapter, hose and securing means are in working positions an irrigating liquid can be introduced throught the cannula and withdrawn through the hose.

2. A combination according to claim 1, wherein the adapter has one or more reinforcing beads, with the side of each bead that faces the end of the adapter sloping toward that end.

3. A combination according to claim 1, wherein the hose is a length of flexible plastic tubing.

4. A combination according to claim 1, further including a waste collector connected to the hose.

5. A combination according to claim 4, wherein the waste collector is integral with the hose.

6. A combination according to claim 1, wherein the means for securing the intestine over the adapter is a rapid fastener, having a row of teeth matching depressions in a channel, which is slightly curved inward, and a tightening tab.

7. In combination, for irrigating the intestines during surgery, an irrigating cannula for connection to the intestines at one location, an adapter for connection to the intestines at a second location, the adapter having on or more trimming guides in the form of scores, means for securing the intestines to said adapter, and a hose connected to the adapter, whereby when said cannula, adapter, hose and securing means are in working positions an irrigating liquid can be introduced through the cannula and withdrawn through the hose.

8. In combination, for irrigating the intestines during surgery, an irrigating cannula for connection to the intestines at one location, an adapter for connection to the intestines at a second location, the adapter having one or more reinforcing beads tapering forwardly toward the intestine-connecting end of the adapter, means for securing the intestines to said adapter, and a hose connected to the adapter, whereby when said cannula, adapter, hose and securing means are in working positions an irrigating liquid can be introduced through the cannula and withdrawn through the hose.

9. In combination an adapter means, an irrigation cannula, a waste collector, and an inlet drainage hose for said waste collector, said adapter means connecting said inlet drainage hose to the intestines to allow for drainage from said irrigating cannula through the intestines and into said waste collector through said adapter means, said adapter means being longitudinally conical and having at least one transverse reinforcing bead and at least one transverse trimming guide in the form of score lines.

* * * * *